Figure 1:
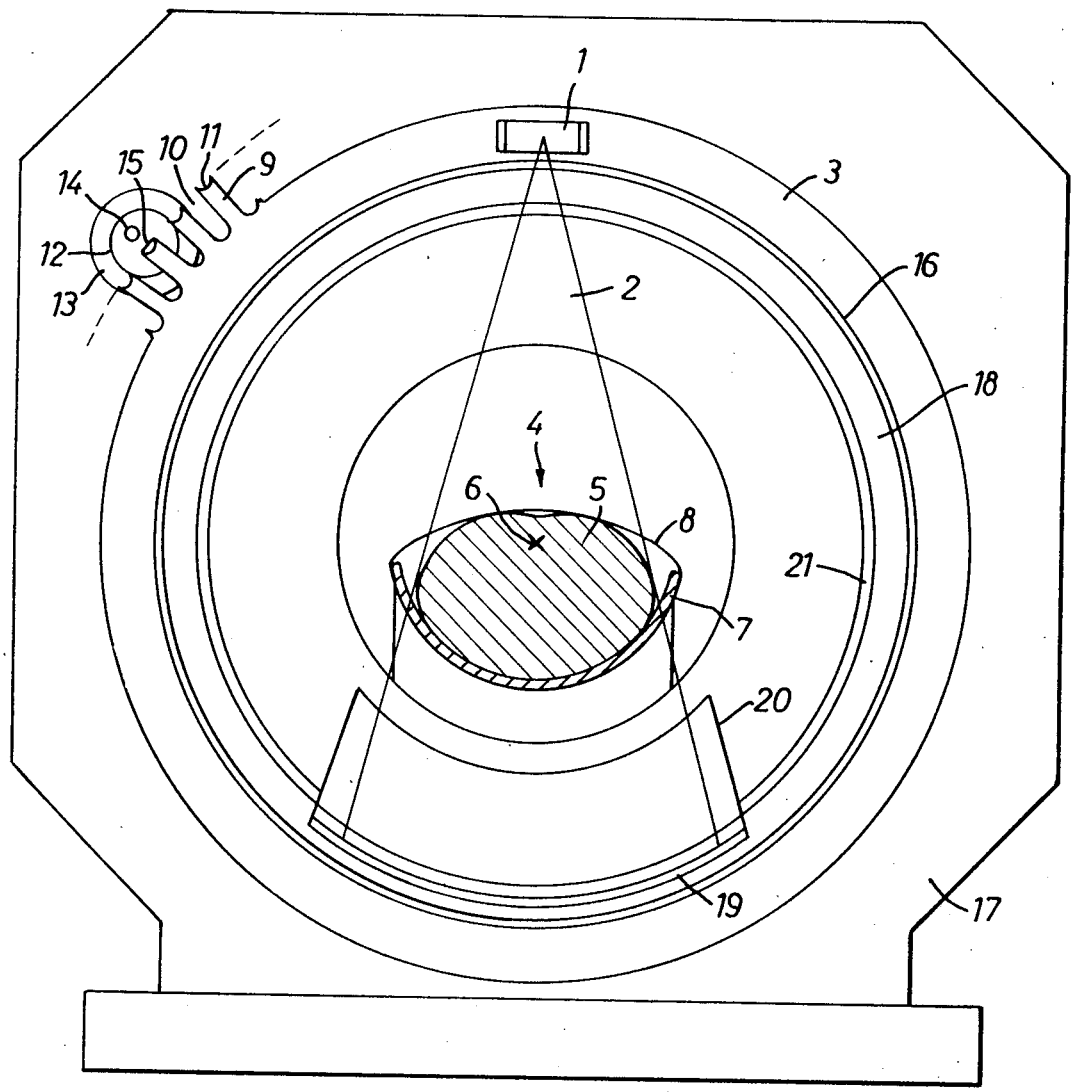

United States Patent [19]

Waltham

[11] 4,171,476
[45] Oct. 16, 1979

[54] RADIOGRAPHY

[75] Inventor: Richard M. Waltham, London, England

[73] Assignee: EMI Limited, Middlesex, England

[21] Appl. No.: 880,009

[22] Filed: Feb. 21, 1978

[30] Foreign Application Priority Data

Feb. 24, 1977 [GB] United Kingdom ............... 7910/77

[51] Int. Cl.² ..................... G01N 21/34; G01N 23/04
[52] U.S. Cl. ................................ 250/445 T; 250/360
[58] Field of Search ........................... 250/445 T, 360

[56] References Cited

U.S. PATENT DOCUMENTS

| 3,778,614 | 12/1973 | Hounsfield | 250/445 T |
| 3,866,047 | 2/1975 | Hounsfield | 250/445 T |
| 3,924,129 | 12/1975 | LeMay | 250/363 |
| 3,946,234 | 3/1976 | Hounsfield | 250/445 T |
| 4,010,370 | 3/1977 | LeMay | 250/445 T |
| 4,034,224 | 7/1977 | Heavens | 250/445 T |
| 4,071,760 | 1/1978 | LeMay | 250/445 T |
| 4,115,698 | 9/1978 | Hounsfield | 250/445 T |

Primary Examiner—Craig E. Church
Assistant Examiner—Thomas P. O'Hare
Attorney, Agent, or Firm—Cooper, Dunham, Clark, Griffin & Moran

[57] ABSTRACT

In a computerized tomographic apparatus in which the source and detectors are moved angularly around the body, the angular movement of the source is, in effect, periodically arrested so that the detectors, which are of greater angular extent than the distribution of radiation produced by the source, slide through the distribution. In this way successive detectors can be made to view the same beam in the distribution.

8 Claims, 4 Drawing Figures

RADIOGRAPHY

The present invention relates to radiography, and it relates more specifically to a branch of radiography which has become known as computerised tomography.

Computerised tomography permits the production of a representation of the variation, over a cross-sectional slice of a body under examination, of the absorption or transmission coefficient with respect to penetrating radiation, such as X-radiation. Such representations provide a considerable amount of clinically useful information and, in particular, enable tumours or tissue damage to be identified and accurately located without the need for surgery or invasive diagnostic procedures.

Various techniques for performing computerised tomography are described in U.S. Pat. No. 3,778,614 and other techniques are disclosed and claimed in (inter alia) U.S. Pat. No. 3,946,234 and in U.S. Pat. No. 4,035,647. These two latter techniques are concerned primarily with the acquisition of the data necessary to permit the desired representation to be produced and the technique disclosed and claimed in U.S. Pat. No. 4,035,647 offers potentially the more rapid data acquisition rate. Rapid data acquisition is of importance, because if the data are acquired rapidly there is less chance of the representation being spoilt or marred by artefacts due to movement of the body under examination, or of organs or fluids therein, during the acquisition time.

In principle, with the technique described and claimed in U.S. Pat. No. 4,035,647 the radiation is constrained to conform to a fan-shaped spread, emanating from a small source area, and the radiation is projected through the body. The fan angle of the spread of radiation is sufficient to embrace at least a substantial part of the aforementioned slice of the body and the source is rotated around the body about an axis intersecting the slice. An array of detector devices is provided to receive radiation projected through the body and to provide output signals which are sampled at a rapid rate to produce individual output signals attributable to respective, substantially linear, beam paths traversed by the radiation through the body.

The array of detector devices may be just sufficient in angular extent to accommodate the aforementioned spread of radiation, and in that case it will be appreciated that the beam paths along which radiation is projected towards any detector will all be tangential to a respective, common circle. Because of this, in some circumstances, the representations obtained after processing the data acquired by the technique just described can be spoilt or marred by artefacts due to sensitivity differences and/or relative changes in sensitivity as between the various detectors.

Techniques have been evolved, and two of these are described in the U.S. Pat. No. 4,010,370 and U.S. Pat. app. Ser. No. 733,941, now U.S. Pat. No. 4,115,698 respectively, for overcoming or reducing the problem described in the last preceding paragraph whilst maintaining the advantage of rapid data cquisition. However these techniques involve the production of considerable amounts of data at rapid rates and the handling of such data can, in some cases, give rise to difficulty.

It is an object of this invention to provide a computerised tomographic apparatus which permits rapid data acquisition and enables representations to be produced which are substantially free of artefacts due to sensitivity differences and/or relative changes in sensitivity as between detectors without, however, requiring the acquisition of data at rates which are too high for convenient handling.

According to the invention from one aspect there is provided radiographic apparatus comprising
  (a) patient locating means
  (b) a source of penetrating radiation (such as X-radiation) arranged to produce a divergent spread of the radiation directed to pass through a patient located by said locating means
  (c) a plurality of detectors for receiving the radiation transmitted through said patient along relatively narrow, angularly spaced beam paths, and for producing signals indicative of the received radiation
  (d) scanning means for
    (i) causing the radiation to assume a series of different angular positions during first periods of time, the origin of the spread remaining effectively stationary during each said first period
    (ii) causing said spread to move from one of said angular positions to the next during second periods of time interleaving said first periods of time so that the spread angularly scans a slice of the patient, the slice being disposed transverse to the axis of the angular movement and
    (iii) causing said detectors to move with respect to said spread during said first intervals of time in such a way that a succession of the detectors receive radiation along each of said beam paths, and
  (d) means for producing a representation of a characteristic of said slice affecting said radiation in response to the signals produced by the detectors.

In one example, the source and the detectors are mounted on a frame which is angularly movable about said axis, and said scanning means includes means for moving said frame smoothly about said axis and for reciprocating the origin of said spread of radiation to periodically effectively arrest the movement of the spread of radiation which would otherwise occur due to said smooth movement of the frame.

In another example, the source comprises means for generating X-radiation at a plurality of locations distributed angularly about said axis, and said detectors are mounted on a frame which is angularly movable about said axis, and said scanning means includes means for stepping the origin of said X-radiation from one of said locations to another and for effecting a smooth angular movement of said frame.

According to the invention from another aspect there is provided radiographic apparatus comprising means for projecting a substantially planar, fan-shaped spread of penetrating radiation, such as X-radiation, across a location at which a selected cross-sectional slice of a body under examination may be located, from each of a plurality of positions distributed angularly around said location, detector means including an array of detector devices disposed to receive said radiation after it has traversed said location, scanning means for causing, on the one hand, said spread of radiation to move, or effectively move, in discrete angular steps around said location and to dwell at each of said angularly distributed positions and, on the other hand, said detector array to perform a smooth angular movement around said location, the movement, or effective movement, of the spread of radiation and the movement of the detector array being such that, whilst the spread dwells in each of said positions, the detector array moves relatively thereto, sequentially aligning a number of different detectors with each angular portion of said spread.

Figure 2:
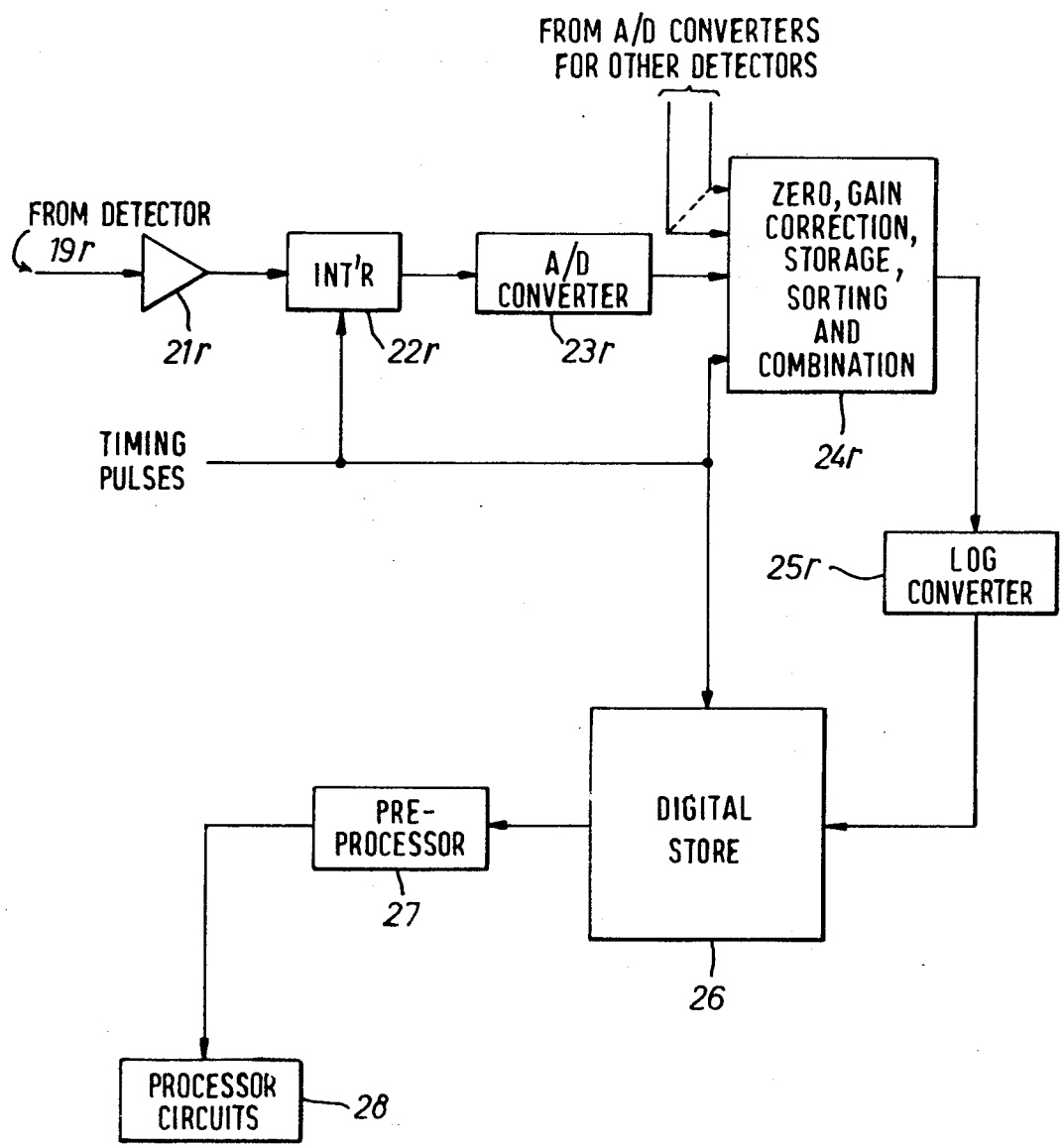
Figure 3:
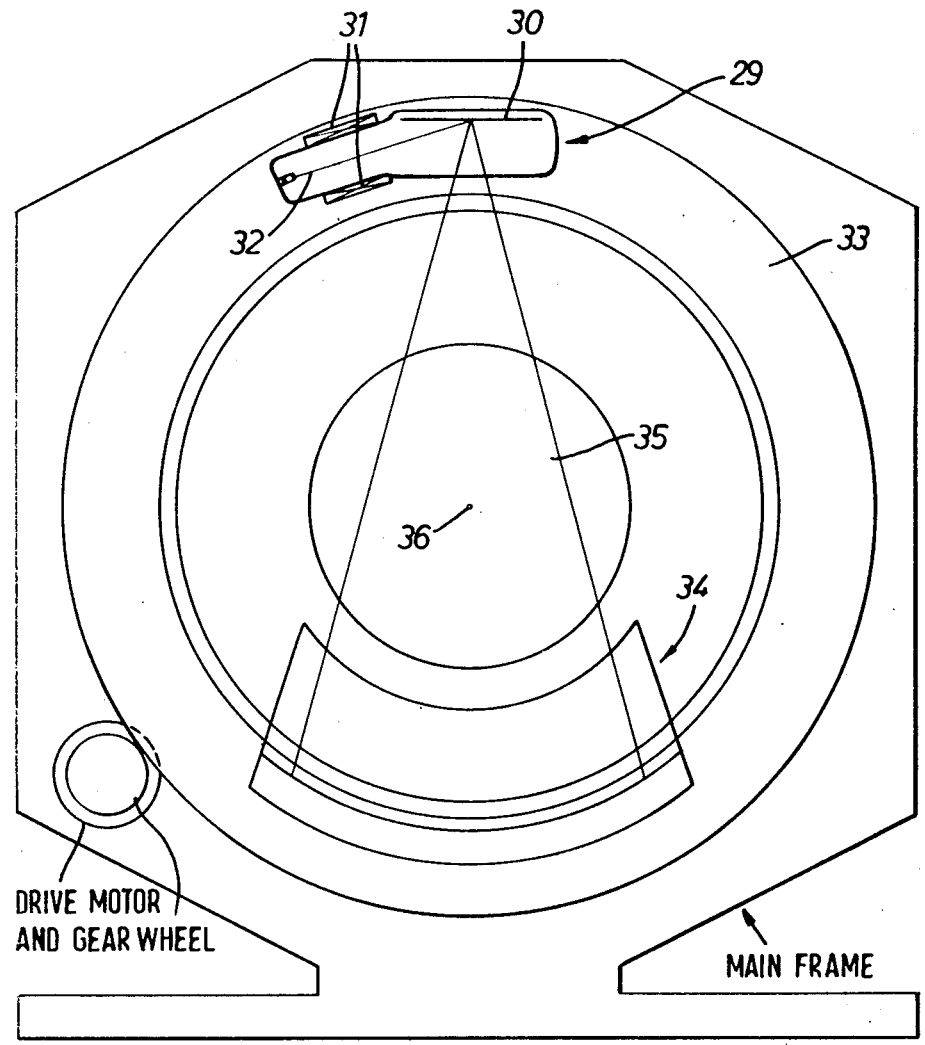

In order that the invention may be clearly understood and readily carried into effect, some embodiments thereof will now be described, by way of example only, with reference to the accompanying drawings, in which:

FIG. 1 shows, in front elevational view, a radiographic apparatus in accordance with one example of the invention, FIG. 2 illustrates, in flow diagrammatic manner, one way in which data produced by the apparatus shown in FIG. 1 can be assembled for processing, FIG. 3 shows, in front elevational view, radiographic apparatus in accordance with a second example of the invention, and FIG. 4 shows, again in front elevational view, radiographic apparatus in accordance with a third example of the invention.

Referring now to FIG. 1, there is shown apparatus in accordance with one example of the invention. This example is described first because, as it involves mechanical drive systems only, it is simpler to visualise than some other examples of the invention. It is not necessarily, however, a preferred form of the invention.

A source 1 of a substantially planar, fan-shaped spread 2 of X-radiation is mounted upon a ring 3 which can rotate in steps around a location 4 in which a selected cross-sectional slice 5 of a patient's body can be disposed. The source 1 can conveniently comprise a rotating anode X-ray generating tube of known kind, and the rotational movement of the ring 3 (and thus of the source 1) around the location 4 is performed about an axis 6 which intersects the slice 5 of the patient's body.

The patient's body is supported supine upon a platter 7 which is slidably supported upon front and rear couches of arcuate form, for example as described in U.S. Pat. No. 4,034,224. The body is held firmly in place on the platter by means of straps such as 8. Gaps between the patient's body and the platter are preferably filled with bags (not shown) containing material which absorbs the X-radiation to substantially the same extent as does human body tissue. The bags may also be placed to the side of and on top of the body so as to form, with the body, a substantially circular object for irradiation.

The stepped rotational movement of the ring 3 around the location 4 is achieved, in this example, by means of a drive mechanism known as a Geneva mechanism. The outer periphery of the ring 3 is formed with prongs such as 9 and slots such as 10; the prongs being formed with arcuate depressions such as 11. A drive wheel 12 is continuously rotated, by means of an electric motor 13, and it carries a pin 14 and a locking cam 15. The pin is mounted eccentrically on the wheel 12 and is disposed so that, upon anticlockwise movement of the wheel 12, the pin enters radially the slot between two prongs, engages one of them and pushes the ring 3 in a clockwise direction through a well defined angle and then leaves the slot radially. In order that the ring 3 is held steady between successive rotational step movements, the cam 15 engages with the depression 10 of the prong which formed one edge of the slot into which the peg has entered and emerged from, but which was not engaged by the peg during the previous rotational step.

The ring 3 is supported on an annular bearing 16 which is secured to a fixed frame member 17. The frame member 17 also supports the aforementioned motor 13 and drive wheel 12.

Disposed inside the ring 3, and mounted concentrically therewith, is a second ring 18 which supports an array 19 of radiation-sensitive detectors. The array may contain a hundred or more detectors, and each detector conveniently comprises, in optical combination, a caesium iodide scintillator crystal and a photo-diode. Other forms of detector may be used if desired, however, without departing from the scope of this invention. The field of view of each detector is defined by a respective collimator, so that, at any given time, it receives radiation projected through the location 4 along a respective substantially linear beam path, and the various collimators are disposed in a bank 20 supported by the ring 18. It will be noted that the array 19 of detectors and the bank 20 of collimators extend beyond the bounds of the spread 2 of X-radiation. This is one important feature of this example of the invention and will be discussed in more detail hereinafter.

The ring 18 is mounted on a bearing 21 which is supported by the frame member 17 and ring 18 is rotated smoothly about the axis 6 by a direct drive (not shown) from the motor 13.

The inter-relationship of the stepped angular movement of ring 3 and the smooth rotation of ring 18 is such that, during the period in which the spread 2 of radiation dwells in each of the angular positions, around location 4, defined by the Geneva mechanism 10–15, the detector array 19 moves through the spread of radiation, in a clockwise direction, from the position in which the extreme left-hand detector of array 19 aligns with the extreme left-hand edge of the spread 2 to the position in which the extreme right-hand detector of the array 19 aligns with the extreme right-hand edge of the spread 2. When the latter-mentioned position has been reached, the Geneva mechanism rotates the ring 3 through the aforementioned well-defined angle, which is chosen to be sufficient to cause the extreme left-hand edge of the spread 2 to catch up with, and again align with, the extreme left-hand detector in the array 19. The above-described process of movement of the array 19 through the spread 2 is then repeated and so-on until a total rotation of at least 180° or at least 180° plus the angle of the fan-shaped spread 2, depending upon the form of processing to be used, has been carried out by the rings 3 and 18.

It will be appreciated that the situation shown in FIG. 1 is that which obtains half-way through the dwell period of the spread 2 in the angular position shown.

The output signals provided by each detector in the array 19 are sampled a number of times during each dwell period of the spread 2 (i.e. during periods when the array 19 moves through the spread 2) so that each detector produces distinguishable output signals relating to a number of mutually divergent beam paths through the location 4 during each of said periods. In this example, there are eight detectors which, at any time, lie outside the bounds of the spread 2 and each detector output is sampled eight times or more during each of said periods. Conveniently, in this example each detector output is sampled sixteen times per period in order to allow data relating to overlapping beams to be derived. Thus, if the spread 2 irradiates a total of n detectors at a time (the array 19 thus consisting of (n+8) detectors), at a given sampling period output signals will be generated from those n detectors in relation to a group of n substantially linear and mutually divergent beam paths through the location 4. At the next-but-one sampling period, output signals will be generated, in respect of the same n beam paths, by (n-1) of the same detectors and one new detector which has now moved into the spread 2. Each of the (n-1) detectors still irradiated by the spread 2 receives radiation along a beam path along which, prior to the previous sampling period, radiation was received by a neighbouring detector. In the course of a complete dwell period, therefore, it will be appreciated that radiation projected along each beam path is received in succession by eight different detectors. In order to reduce the effects of interdetector sensitivity variations, therefore, the eight output signals pertaining to each path are combined. For convenience, the combined signals can be divided by eight to effect an averaging of contributions from different detectors.

If desired, the aforementioned eight output signals pertaining to a given path can be compared to assess differential errors, corrected for such errors (taking one of the detectors as a master to which the others are normalised) and then combined. Usually, however, mere combination is sufficient.

If the detectors are numbered D1, D2, D3 etc. starting from the left in FIG. 1, then it will be clear that the net output signal pertaining to the beam path traversed through the location 4 by radiation at the extreme left-hand edge of spread 2 will be one-eighth of the sum of the output signals produced by detectors D1–D8 when aligned with that beam path during the dwell time of the spread 2 in the angular position shown in FIG. 1. Likewise, the output signal for the beam path, through the location 4, traversed by radiation adjacent the left-hand edge of spread 2 will be one-eighth of the sum of the signals obtained from detectors D2–D9 when aligned with a common beam path during the same dwell time and so-on. If the aforementioned normalisation is effected, and if detector D1 is regarded as the master, then since detectors D2 to D8 are corrected with reference to detector D1, it will be appreciated that detector D9 can also be corrected with reference to detector D1 and so can all of the other detectors; the corrections being in effect, passed on from one detector group to another across the array.

It will be appreciated that the respective beam paths followed by the radiation towards the n detectors which, for the time being, are irradiated by the spread 2 of radiation are mutually divergent; the angle $\beta$ between the centre-lines of adjacent beam paths being $\alpha/n$, where $\alpha$ represents the angle subtended at the detector array by the spread 2 (typically 30° to 40°).

The Geneva mechanism described hereinbefore can be arranged to rotate the spread in steps of $m\beta°$, where m is an integer. Clearly, if m takes the value unity, then (n-1) of the beam paths in respect of which output signals are obtained during one dwell period will be parallel to beam paths in respect of which output signals were obtained during the previous dwell period. In that case, rotation of the spread (in steps of $\beta°$) through a considerable angle (in excess of $\alpha°$) enables output signals to be obtained in respect of a set of parallel beam paths at each of a number of angles with respect to the location 4, neighbouring sets of paths being spaced in angle by $\beta°$.

Clearly if m takes a value greater than unity then the number of beam paths in each set is reduced, but provided m does not exceed n no set will be totally lost. In practice, however, it is unusual for m to exceed ten when n takes a value around one hundred, because the loss of beam paths in each set tends to reduce the resolution of the apparatus beyond acceptable levels if m exceeds ten.

Modifications may be made to the apparatus shown in FIG. 1 without departing from the scope of the invention. For example the spread 2 may be sectioned up into individual beams prior to its incidence upon the body slice 5 by a suitable array of collimators (not shown) aligned with the array 19. Moreover, shaped attenuators may be placed between the source and the body and/or between the body and the detector array for the purpose of tending to equalise the absorption suffered by the radiation at all points across the spread 2.

In known manner, graticules (not shown) are formed on, or carried by, the rings 3 and 18 and these graticules cooperate with respective photo-cell units to permit the progress of the angular movements of the rings to be monitored by virtue of timing pulses generated by the photo-cell units. These timing pulses are used to effect the sampling of the detector output signals, as referred to hereinbefore, to verify the synchronism between the stepped rotation of ring 3 and the smooth rotation of ring 18 and to control the distribution of the sampled detector output signals amongst storage addresses of digital storage means.

FIG. 2 indicates a flow diagram in respect of one detector, the r'th detector, in the array 19. The detector 19r feeds an amplifier 21r, and thence an integrator 22r which, in known manner, is read and reset periodically by means of the timing pulses derived from the graticule associated with the ring 18. This periodic reading and resetting of the integrator 22r effects the aforementioned sampling of the detector output signals and is carried out, in this example, eight times during each dwell period of the spread 2. It will be appreciated that the movement of spread 2 from one of its dwell positions to the next is not instantaneous, and it is preferable for the sampling of the integrators such as 22r to be continued during the angular movement of the ring 3 with the radiation, however, interrupted. This enables zero level checks to be made on the detectors (i.e. to check whether the detectors are providing output signals of finite amplitude when, because the radiation is interrupted they should be producing no output signals) and permits allowance to be made for after glow in the crystals. After glow is a term commonly used in this art to describe a phenomenon known as phosphorescene which manifests itself as a lag in the response of the detector devices, causing (if uncorrected) an output signal provided in respect of one path to be contaminated by portions of the radiation previously transmitted to the detectors along one or more other paths. All of the integrators such as 22r are read and reset simultaneously.

The sampled output signals from the integrator 22r are applied to an analogue-to-digital converter circuit 23r of known kind, to zero and-gain correction circuit, a short term store, sorting and combining circuits, all of which are included in a circuit 24r, and thence to a logarithmic converting circuit 25r, of known kind. Each signal from the circuit 25r relates to a respective beam path through the location 4. The signal is thus routed, under the influence of the timing pulses derived from the graticules associated with both rings, 3 and 18, (because the beam concerned is characterised by the angular position of the spread 2 as well as the position of the detector array 19 relative to the spread at the relevant sampling time) to a storage address in a digital store 26 which has a storage address dedicated to each beam path.

It will be realised that if detector 19r has provided an output signal relating to a given beam path at one sampling time then (provided there is another sampling time within the relevant dwell period of spread 2), the next sampling time will result in detector 19r+1 providing an output signal in respect of the same beam path. That output signal is routed to the circuit 24r for combination with the output signal from detector 19r which was derived at the previous sampling time. Thus, in the course of rotation of the rings 3 and 18 through at least an angle of (180°+α°) in this example, each address of the store 26 is supplied with a combination of (in this example) eight digitised output signals. The signals distributed to a respective address are, if necessary, divided by eight to average them. The division by eight, if performed at all, need not be performed in the store 26 but can be effected by separate circuits (not shown) external thereof. The storage addresses in store 26 are conveniently arranged in rows and columns, and each row relates to a set of parallel beam paths; the columns relating to differing positions (measured perpendicularly from the axis 6) of the centre lines of the beam paths in the parallel sets. The sorting of data, derived in groups relating to divergent beam paths, into sets relating to parallel beam paths is disclosed in U.S. patent application Ser. No. 544,799 filed Jan. 28, 1975.

It is known that the spacing of the centre lines of the beam paths in each parallel set varies with position across the set, and a pre-processing circuit 27 is provided to employ any known technique, such as interpolation, to tend to equalise the said spacing. Such interpolation is described in the aforementioned U.S. Pat. No. 4,115,698.

The data, now assembled in groups relating to sets of parallel beam paths, the centre lines of which are equally spaced, are then processed in a processing circuit 28 which may, for example, comprise the arrangement described and claimed in U.S. Pat. No. 3,924,129 in order to produce a representation of the variation of absorption coefficient, with respect to the X-radiation used, over the body slice 5.

It is possible, for example by employing a processing technique of the kind described in U.S. Pat. No. 3,778,614 to process the data, in the form in which they are derived (as fan sets) and, in that case, the parallel set sorting and the interpolation are not required.

FIG. 3 shows another example of apparatus in accordance with the invention. In this case, the X-radiation is produced by a source tube 29 which has an elongated X-ray producing anode 30 and is provided with deflection coils 31 enabling the electron beam 32 of the tube to be scanned along the anode 30. The scanning of the beam 32 along the anode 30 is synchronised with the smooth rotation of a single ring 33, which carries both the source 29 and a detector/collimator assembly 34, so that the origin of the spread 35 of X-radiation stays in one place whilst the ring 33 rotates through a given angle, as before, and then moves rapidly to a new angular position relative to the rotation axis 36. The scanning of the beam along the anode 30 thus is required to counteract exactly the rotation of the ring 33 during each dwell time of the spread 35 and then to fly back rapidly, in the direction of rotation of the ring 33 so that the spread 35 catches up with the leading detector in the assembly 34.

The actual beam paths which can be examined using the technique described with reference to FIG. 3 and the manner in which output signals relating to said beam paths are operated upon and processed can conveniently be the same as described with reference to FIGS. 1 and 2. An additional advantage of the FIG. 3 arrangement, however, is that the X-rays can conveniently be suppressed during the flyback periods of the deflection waveforms applied to the coils 31 and the detector outputs can be sampled at such times to enable the "after-glow" or lag of the detectors to be assessed and compensated for.

The resolution of the representation to be finally produced typically requires the angle $\beta$, or $(\alpha/n)$, between the centre-lines or adjacent beam paths to be $(1/15)°$, but other angles could be used if desired.

Figure 4:
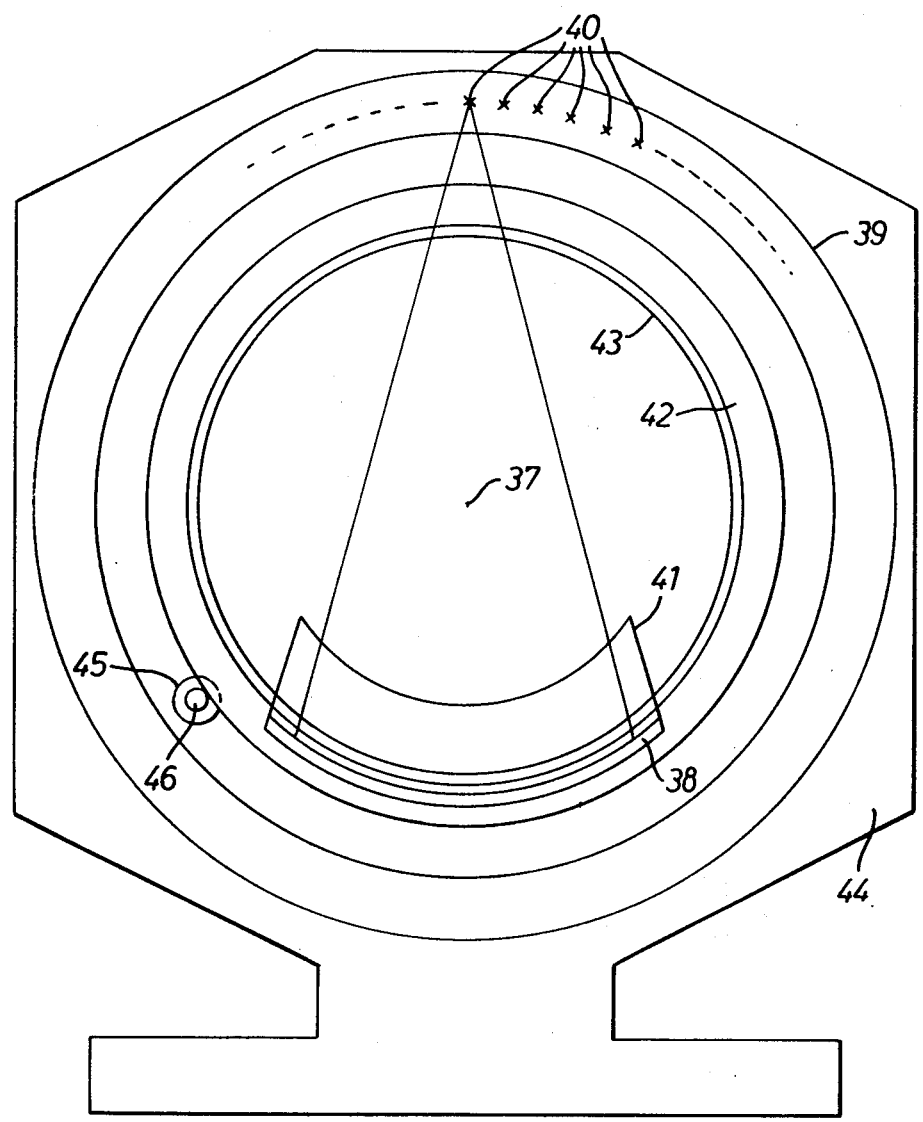

FIG. 4 shows another example of the invention, in which the stepped angular movement of the spread of radiation is achieved by sequential energisation of a number of fan source positions distributed, with the required angular separation, around the rotational axis 37 of a detector array 38. In this example, the required number of static source positions are provided by means of a static, toroidal X-ray tube 39 with multiple X-ray emitting anodes 40 spaced at the requisite angular intervals therearound. The anodes are sequentially caused to emit radiation while the detector array 38 and an associated collimator bank 41 rotate smoothly. It will be appreciated that the detectors and the source may need to be in different planes, but this does not substantially effect the representation produced. Alternatively, as shown in the drawing, the detectors may rotate within the locus of the source points. The array 38 and the collimator bank 41 are supported on a ring 42 which can rotate on a fixed bearing 43 supported by a main frame 44. The rotation of ring 42 is conveniently achieved by means of an electric motor 45, supported by the frame 44, which drives a gear wheel 46, wheel 46 cooperates with gear teeth (not shown) formed all around the outer periphery of ring 42. Each anode 40 can have associated therewith a respective, fixed cathode. In that case, the cathodes can be energised sequentially to direct electron beams, for a desired duration, onto their respective anodes.

Advantages of the arrangement of FIG. 4 over the previously described arrangements include the absence of high power rotating cables or slip rings to convey power or coolant (as the case may be) to the X-ray source and improved dissipation of waste heat generated by the X-ray emission.

In an alternative arrangement to that shown in FIG. 4, the X-ray emissive anodes can be disposed at greater angular spacing. The detectors can then rotate smoothly through one revolution with the tube stationary and the anodes pulsed in sequence as before. The toroid is then rotated (e.g. by a Geneva mechanism) through a small angle and another revolution performed by the detectors. The sequence is continued until the indexing of the toroidal tube has filled the angular gaps between the anode spacings.

It will be appreciated that, in either of the arrangements just described, the beam paths in respect of which output signals are produced, and the manner in which those output signals are treated and processed can be substantially the same as that described in relation to FIGS. 1 and 2.

For accurate processing it is desirable that the source and detectors are mounted on the circumference of a common circule. The centre of this circle is not necessarily, however, the axis of rotation of the apparatus.

In all of the foregoing embodiments of the invention, the ability exists to compensate, by calibration, errors due, for example, to different path lengths followed by the radiation through material, such as the shaped attenuators referred to previously. The calibration is effected by substituting a phantom of known characteristics for the body and obtaining calibration signals which compensate for errors in the evaluation of said characteristics. These calibration signals are stored in known manner, in lock-up tables or in the various locations of a store such as 26.

What I claim is:

1. Radiographic apparatus comprising
   (a) patient locating means
   (b) a source of penetrating radiation (such as X-radiation) arranged to produce a divergent spread of the radiation directed to pass through a patient located by said locating means
   (c) a plurality of detectors for receiving the radiation transmitted through said patient along relatively narrow, angularly spaced beam paths, and for producing signals indicative of the received radiation
   (d) scanning means for
      (i) causing the radiation to assume a series of different angular positions during first periods of time, the origin of the spread remaining effectively stationary during each said first period
      (ii) causing said spread to move from one of said angular positions to the next during second periods of time interleaving said first periods of time so that the spread angularly scans a slice of the patient, the slice being disposed transverse to the axis of the angular movement and
      (iii) causing said detectors to move with respect to said spread during said first intervals of time in such a way that a succession of the detectors receive radiation along each of said beam paths, and
   (d) means for producing a representation of a characteristic of said slice affecting said radiation in response to the signals produced by the detectors.

2. Apparatus according to claim 1 including a frame, on which said source and said detectors are mounted, and means for moving said frame angularly about said axis.

3. Apparatus according to claim 2 wherein said scanning means includes means for moving said frame smoothly about said axis and for reciprocating the origin of said spread of radiation to periodically effectively arrest the movement of the spread of radiation which would otherwise occur as a result of the smooth movement of said frame.

4. Apparatus according to claim 1 wherein said source comprises means for generating X-radiation at a plurality of spaced locations distributed angularly about said axis, the apparatus including a frame, on which said detectors are mounted, and means for moving said frame angularly about said axis and said scanning means including means for causing said radiation to originate in sequence from a plurality of said locations while moving said frame smoothly about said axis.

5. Radiographic apparatus comprising means for projecting a substantially planar, fan-shaped spread of penetrating radiation, such as X-radiation, across a location at which a selected cross-sectional slice of a body under examination may be located, from each of a plurality of positions distributed angularly around said location, detector means including an array of detector devices disposed to receive said radiation after it has traversed said location, scanning means for causing, on the one hand, said spread of radiation to move, or effectively move, in discrete angular steps around said location and to dwell at each of said angularly distributed positions and, on the other hand, said detector array to perform a smooth angular movement around said location, the movement, or effective movement, of the spread of radiation and the movement of the detector array being such that, whilst the spread dwells in each of said positions, the detector array moves relatively thereto, sequentially aligning a number of different detectors with each angular portion of said spread.

6. A computerized tomographic scanner having a spread of X-radiation and a detector array angularly movable around a body under examination; the spread originating in sequence from each of a plurality of discrete origin locations angularly distributed around the body and dwelling at each of said locations for a predetermined time and the detector array moving smoothly around the body causing
   (a) the detector array to smoothly overtake the spread during the times when said spread dwells at each location, taking the relative angular positions of the array and the spread from an initial relative position, at the start of a dwell period, when each beam of the spread aligns with a respective detector of the array, through intermediate relative positions when the beams sequentially align with different detectors, to final position, at the end of a dwell period, when each beam is aligned with a respective further detector, and
   (b) the spread to rapidly overtake the detector array, in moving from one of said locations to the next, to restore the original relative position between said spread and said array.

7. A scanner according to claim 6 wherein the detector array comprises a contiguous array of detector devices extending beyond the bounds of the spread of radiation.

8. A scanner according to claim 7 including means for deriving from said detector devices output signals indicative of the amounts of radiation transmitted thereto along the various beams of the fan and means for combining the output signals from different detectors relating to the same beam and obtained during the same dwell period.

* * * * *